(12) United States Patent
Paranjape

(10) Patent No.: US 10,004,434 B1
(45) Date of Patent: Jun. 26, 2018

(54) MICROFLUIDIC SYSTEMS FOR ELECTROCHEMICAL TRANSDERMAL ANALYTE SENSING USING A CAPILLARY-LOCATED ELECTRODE

(71) Applicant: Georgetown University, Washington, DC (US)

(72) Inventor: Makarand Paranjape, Silver Spring, MD (US)

(73) Assignee: Georgetown University, Washington, DC (US)

( * ) Notice: Subject to any disclaimer, the term of this patent is extended or adjusted under 35 U.S.C. 154(b) by 709 days.

(21) Appl. No.: 13/834,199

(22) Filed: Mar. 15, 2013

(51) Int. Cl.
*A61B 5/145* (2006.01)
*A61B 5/1477* (2006.01)
*A61B 5/1491* (2006.01)

(52) U.S. Cl.
CPC ........ *A61B 5/14532* (2013.01); *A61B 5/1477* (2013.01); *A61B 5/1491* (2013.01)

(58) Field of Classification Search
CPC .............. A61B 5/14532; A61B 5/1486; A61B 5/14521; G01N 33/66
See application file for complete search history.

(56) References Cited

U.S. PATENT DOCUMENTS

| 4,526,176 A | 7/1985 | Bremer et al. ................. 600/392 |
| 4,775,361 A | 10/1988 | Jacques et al. ................ 604/20 |
| 4,821,733 A | 4/1989 | Peck ............................ 128/636 |
| 4,909,256 A | 3/1990 | Peck ............................ 128/632 |
| 5,123,902 A | 6/1992 | Muller et al. ................... 604/21 |
| 5,176,881 A | 1/1993 | Sepaniak et al. ............... 422/82 |
| 5,203,327 A | 4/1993 | Schoendorfer et al. ....... 128/632 |
| 5,330,527 A | 7/1994 | Montecalvo et al. ......... 607/152 |
| 5,362,307 A | 11/1994 | Guy et al. ........................ 604/20 |
| 5,380,272 A | 1/1995 | Gross .............................. 604/20 |
| 5,422,246 A * | 6/1995 | Koopal ................... A61L 31/10 204/403.1 |
| 5,458,140 A | 10/1995 | Eppstein et al. .............. 600/573 |
| 5,591,139 A | 1/1997 | Lin et al. ....................... 604/264 |

(Continued)

FOREIGN PATENT DOCUMENTS

| JP | H01-158343 | 6/1989 | ............. G01N 27/30 |
| JP | H05-172815 | 7/1993 | ............ G01N 33/543 |

(Continued)

OTHER PUBLICATIONS

Paranjape, Makarand, "Pain-Free Diabetic Monitoring Using Transdermal Patches," SPIE Newsroom, 2008. 2 pp.

(Continued)

*Primary Examiner* — Patricia Mallari
*Assistant Examiner* — Michael Catina
(74) *Attorney, Agent, or Firm* — Dawn-Marie Bey; Bey & Cotropia PLLC

(57) ABSTRACT

A sensing device, designed to be used in contact with the skin, contains a plurality of individually controllable sites for electrochemically monitoring an analyte, such as glucose, in interstitial fluid of a user. The device includes at least a hydrophobic layer designed to contact the skin; a capillary channel providing an opening adjacent the skin; a metal electrode layer having a sensor layer applied to an edge portion thereof such that it is exposed to the interior of said capillary channel, the sensing layer being effective to measure the analyte.

10 Claims, 1 Drawing Sheet

(56) References Cited

U.S. PATENT DOCUMENTS

| | | | |
|---|---|---|---|
| 5,722,397 A | 3/1998 | Eppstein | 128/633 |
| 5,730,714 A | 3/1998 | Guy et al. | 604/20 |
| 5,801,057 A | 9/1998 | Smart et al. | 436/68 |
| 5,885,211 A * | 3/1999 | Eppstein et al. | 600/309 |
| 6,056,738 A | 5/2000 | Marchitto et al. | 606/2 |
| 6,124,597 A | 9/2000 | Shehada et al. | 250/461.2 |
| 6,233,471 B1 | 5/2001 | Berner et al. | 600/345 |
| 6,312,393 B1 | 11/2001 | Abreu | 600/558 |
| 6,393,318 B1 | 5/2002 | Conn et al. | 604/20 |
| 6,464,687 B1 | 10/2002 | Ishikawa et al. | 604/891.1 |
| 6,730,212 B1 | 5/2004 | Yamagishi et al. | |
| 6,887,202 B2 | 5/2005 | Currie et al. | 600/309 |
| 7,344,499 B1 | 3/2008 | Prausnitz et al. | 600/309 |
| 7,655,477 B1 | 2/2010 | Schneider et al. | |
| 7,888,509 B2 | 2/2011 | Wolf et al. | |
| 7,931,592 B2 | 4/2011 | Currie et al. | 600/309 |
| 2003/0225362 A1 | 12/2003 | Currie et al. | |
| 2005/0182307 A1 | 8/2005 | Currie et al. | |
| 2006/0115857 A1 | 1/2006 | Keen | |
| 2007/0027383 A1 * | 2/2007 | Peyser et al. | 600/347 |
| 2009/0308742 A1 | 12/2009 | Paranjape | |
| 2011/0042225 A1 | 2/2011 | Monash et al. | |
| 2012/0010487 A1 | 1/2012 | Currie et al. | |
| 2012/0060589 A1 * | 3/2012 | Gridelet et al. | 73/61.61 |
| 2012/0150004 A1 * | 6/2012 | Currie | A61B 5/1486 600/347 |

FOREIGN PATENT DOCUMENTS

| | | | |
|---|---|---|---|
| JP | H07-000541 | 1/1995 | A61N 1/36 |
| JP | H09-140687 | 6/1997 | A61B 5/14 |
| WO | WO 97/42882 | 11/1997 | A61B 17/14 |
| WO | WO 99/44507 | 9/1999 | A61B 10/00 |
| WO | WO 99/58050 | 11/1999 | A61B 5/00 |
| WO | WO 00/04832 | 2/2000 | A61B 10/00 |
| WO | WO 00/15102 | 3/2000 | A61B 5/00 |
| WO | WO 09/025698 | 2/2009 | |
| WO | WO 2009/121041 A2 | 10/2009 | G01N 35/00 |

OTHER PUBLICATIONS

International Search Report and Written Opinion for Application No. PCT/US14/19183, dated May 14, 2014, 7 pp.

Paranjape et al. "A PDMS dermal patch for non-intrusive transdermal glucose sensing" Sens. Actuat. A; 2003; vol. 104; p. 195-204 (2003), Entire Document.

Connolly et al. "Minimally Invasive Sensing" Ch 18, of "Biosensors—Emerging Materials and Applications"; Jul. 2011; ISBN: 978-953-307-328-6; p. 355-382 (Jul. 2011), entire documents [online]; download from: <http://cdn.intechweb.org/pdfs/16435.pdf> on Mar. 30, 2013.

PCT Communication for application No. PCT/US2013/27126 filed Feb. 21, 2013, "Notification of the International Search Report and the Written Opinion of the International Searching Authority, or the Declaration", dated Apr. 26, 2013.

Preliminary Examination Report for Application No. PCT/US01/17081, dated Sep. 15, 2004 (mailing date).

International Search Report, dated Aug. 14, 2001.

"SpectRx An Innovactive Medical Technology Company" [online], Copyright 2004 [retrieved on Aug. 31, 2004], 1 p., Retrieved from the Internet: http://www.spectrx.com.

Written Opinion for Application No. PCT/US01/17081, dated Feb. 13, 2004 (mailing date).

Schneider, T., et al., "B-Fit μSystem: Bio-Flips Integrable Transdermal MicroSystem," *ARO Workshop on Biomolecular Signaling, Energy, Transfer, and Transduction Processes*, Cashiers, NC, May 14-17, 2000, 16 pp.

Smith, Frederick P. and Kidwell, David A., "Cocaine in Hair, Saliva, Skin Swabs, and Urine of Cocaine Users' Children," *Forensic Science International*, vol. 83, pp. 179-189, 1996.

Balabanova, Von Svetla and Schneider E., "Detection of Drugs in Sweat (Nachweis von Drogen im Schweiβ)," *Beitr. Gerichtl. Med.*, vol. 48, pp. 45-49, 1990.

Peck, Carl C., et al., "Outward Transcutaneous Chemical Migration: Implications for Diagnostics and Dosimetry," *Skin Pharmacol.*, vol. 1, No. 1, pp. 14-23, 1988.

Phillips, Michael and McAloon, Margaret H., "A Sweat-Patch Test for Alcohol Consumption: Evaluation in Continous and Episodic Drinkers," *Alcohol: Clinical and Experimental Research*, vol. 4, No. 4, pp. 391-395, 1980.

Henderson, Gary L. and Wilson, B. Kent, "Excretion of Methadone and Metabolites in Human Sweat," *Research Communications in Chemical Pathology and Pharmacology*, vol. 5, No. 1, pp. 1-8, Jan. 1973.

Supplementary European Search Report for Application No. EP 01 93 9501, dated Jan. 11, 2011.

Zhang, et al., J. Matl. Sci. Matls. in Medicine 16 (2005), pp. 933-946.

Martinez, et al., PNAS 105(5), 19606-19611 (2008).

Martinez, et al., Anal. Chem., 82:3-10 (2010).

Abe, et al., Analyt. Chem. 80 (2008) (6928-6934).

Li, et al., Analyt. Chem. 80 (2008) (9131-9134).

Chronakis, et al., Polymer 47(5):1597-1603 (2006).

Miao, et al., J. Nanosci. Nanotech. 10:5507-5519 (2010).

Shiroma, et al., Analytica Chimica Acta 725 (2012 (44-50).

Dungchai, et al., Analyt. Chem. 81 (2009), 5821-5826.

Liu, et al., Matl. Sci. Eng. C27(1):57-60 (Jan. 2007).

Yamada, et al., Chem. Lett. 26(3):201-202 (1997).

Fortier, et al., Biosens. Bioelectronics 5:473-490 (1990).

International Search Report and Written Opinion for Application No. PCT/US14/11296, 6 pp., dated Feb. 25, 2015.

Kastantin, Mark J., et al., "Integrated Fabrication of Polymeric Devices for Biological Applications," Sensors and Materials, vol. 15, No. 6, pp. 295-311, 2003.

Gadre, A. P., et al., "Fabrication of a Fluid Encapsulated Dermal Patch Using Multilayered SU-8," Sensors and Actuators A 114, pp. 478-485, 2004.

Nira R. Pollock, et al., "A Paper-Based Multiplexed Transaminase Test for Low-Cost, Point-of-Care Liver Function Testing," Sci. Transl. Med. 4, 152ra129 (2012), 11 pp.

Jan Lankelma, et al., "Paper-Based Analytical Device for Electrochemical Flow-Injection Analysis of Glucose in Urine," Analytical Chemistry, 84, pp. 4147-4152, 2012.

\* cited by examiner

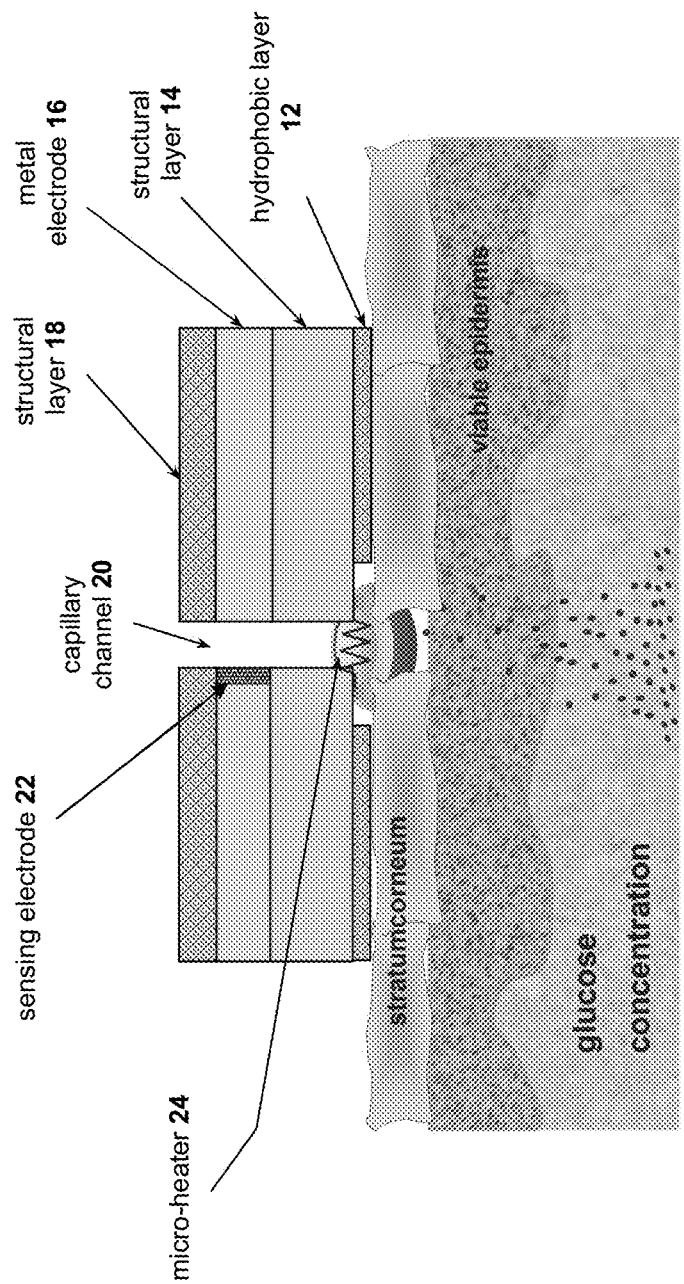

MICROFLUIDIC SYSTEMS FOR ELECTROCHEMICAL TRANSDERMAL ANALYTE SENSING USING A CAPILLARY-LOCATED ELECTRODE

FIELD OF EMBODIMENTS

The present embodiments relate generally to non-invasive or minimally invasive transdermal measurement systems. More specifically, the embodiments relate to microfluidic transdermal glucose measurement systems in which a thin electrode is contained within a fluid-transmitted capillary, and processes for their production and use.

BACKGROUND

Minimally invasive transdermal systems are described in, for example, co-owned U.S. Pat. Nos. 6,887,202 and 7,931,592, both entitled "Systems and Methods for Monitoring Health and Delivering Drugs Transdermally," as well as co-owned U.S. application Ser. No. 13/459,392, each of which is incorporated herein by reference in its entirety. These systems, like the embodiments described herein, provide for a minimally invasive sampling technique and device suitable for rapid, inexpensive, unobtrusive, and pain-free monitoring of important biomedical markers, such as glucose.

Existing systems remain open to improvement in various aspects, including consistency in sampling and measurement.

SUMMARY

A sensing device, designed to be used in contact with the skin, is provided. The device contains a plurality of individually controllable sites for electrochemically monitoring an analyte, such as glucose, in interstitial fluid of a user. The device includes:
 a hydrophobic layer, designed to contact the skin;
 an overlaying first structural layer;
 an overlaying metal electrode layer;
 an overlaying second structural layer;
 for each such detection site, a capillary channel traversing these layers, thus providing an opening adjacent the skin;
 wherein said metal electrode layer is discontinuous at the circumference of said capillary channel, such that two non-contiguous edge portions of electrode are present within the circumference of said channel;
 applied to one such edge portion of the metal electrode layer, such that it is exposed to the interior of said capillary channel, a sensing layer effective to measure said analyte; and surrounding the lower end of said capillary channel, adjacent said hydrophobic layer, an electronic element (microheater) effective to produce heat when a sufficient voltage is applied thereto.
 Also provided are electrical conduits and contacts such that a voltage can be applied to the microheater, and an additional voltage can be applied between the two edge portions of the electrode layer, and an electrochemical response from the sensing material/electrode layer, indicative of the concentration of analyte in the sample fluid, can be detected.

In selected embodiments, the hydrophobic layer is hydrophobic silicone. The first structural layer may be a glass or ceramic-like material. The metal electrode layer is preferably gold or platinum, and the sensing layer, for use in detecting glucose, is preferably a conducting polymer, such as polypyrrole (PPy), modified with glucose oxidase (GOx), and preferably further containing an effective amount of a mediator such as ferricyanide. The second structural layer is preferably non-absorbent and/or hydrophobic, and may also be a layer of hydrophobic silicone.

The diameter of the capillary channel, in one embodiment, is about 50 μm.

The thickness of the metal electrode layer is generally in the range of 100 nm to 1 micron range, e.g. 100-500 nm, 500-1000 nm, 500-800 nm, 250-750 nm, 300-500 nm, etc. An exemplary thickness is about 500 nm. The structural layers generally have thicknesses such that the overall thickness of the device is about 1 mm or less.

The thickness of the applied sensing layer, measured in a direction perpendicular to the capillary channel length, may be 200 nm or less, 100 nm or less, or 50 nm or less, in selected embodiments.

In use, a voltage is applied to the microheater sufficient to ablate the stratum corneum of the underlying skin, e.g. a voltage of about 3 V, typically for about 30 msec. This ablation allows interstitial fluid to enter the capillary channel, where it rises via both capillary action and the body's hydrostatic pressure and contacts the sensing material (e.g. PPy/GOx) within the capillary. A second voltage, typically 0.2-0.4 V, is applied to the electrode layer, i.e. between the two above-described edge portions of the electrode layer, and the level of analyte (e.g. glucose) contacting the sensing material is electrochemically detected, in accordance with known methods.

BRIEF DESCRIPTION OF THE DRAWING

FIG. 1 illustrates an embodiment of a sensing device as disclosed herein.

DETAILED DESCRIPTION

A section of an exemplary sensing device, designed to be used in contact with the skin, is shown in FIG. 1. The device typically contains a plurality of individually controllable sites, of which one is illustrated in the FIGURE, for electrochemically monitoring an analyte, such as glucose, in interstitial fluid of a user. The device, in a preferred embodiment, includes:
 a hydrophobic layer 12, designed to contact the skin;
 an overlaying first structural layer 14;
 an overlaying metal electrode layer 16;
 an overlaying second structural layer 18;
 a capillary channel 20 traversing these layers, thus providing an opening adjacent the skin;
 wherein said metal electrode layer is discontinuous at the circumference of said capillary channel, such that two non-contiguous edge portions of electrode are present within the circumference of said channel;
 applied to one such edge portion of the metal electrode layer, such that it is exposed to the interior of said capillary channel, a sensing layer 22 effective to measure said analyte; and surrounding the lower end of said capillary channel, adjacent said hydrophobic layer, an electronic element (microheater) 24, effective to produce heat when a sufficient voltage is applied thereto.

The diameter of the capillary channel, in one embodiment, is about 50 μm.

The thickness of the metal electrode layer is generally in the range of 100 nm to 1 micron range, e.g. 100-500 nm, 500-1000 nm, 500-800 nm, 250-750 nm, 300-500 nm, etc.

An exemplary thickness is about 500 nm. The thickness of the structural layers is not generally critical (although layer 12 should be sufficiently thick to insulate sensing material 22 from heat produced by microheater 24), but these may also be in the general range of hundreds of nm, e.g. 100-500 nm, 500-1000 nm, 500-800 nm, 250-750 nm, 300-500 nm, etc. The overall thickness of the device is generally less than 1 mm.

The diameter of the capillary channel 20, in one embodiment, is about 50 μm. Other diameter ranges, e.g. 10-100 μm, or 25-75 μm, could also be effective.

Also provided, though not shown in the FIGURE, are electrical conduits and contacts such that a voltage can be applied to the microheater, and an additional voltage can be applied to the electrode layer (i.e. between the two above-described edge portions of the electrode layer), and an electrochemical response from the sensing material/electrode layer, indicative of the concentration of analyte in the sample fluid, can be detected. The multiple detection sites within a device are preferably individually controllable; i.e. voltages can be selectively applied to a given detection site or sites by a user of the device.

In selected embodiments, the hydrophobic layer 12 is hydrophobic silicone, though any biocompatible/non-irritating hydrophobic material can be used. The structural layer 14 may be a glass or ceramic-like material, which provides thermal insulation between the microheater 24 and sensing material 22, or other structurally stable, nonabsorbent, preferably thermally insulating material. The metal electrode layer 16 is preferably gold or platinum.

A sensing layer 22 effective to measure the analyte is present on one of the above-described edge portions of the metal electrode layer, such that it the sensing material is exposed to the interior of the capillary channel. The sensing layer 22, for use in detecting glucose, is preferably a conducting polymer, such as polypyrrole (PPy), modified with the enzyme glucose oxidase (GOx).

Preferably, in fabrication, the PPy-GOx layer is electrodeposited, in accordance with known methods (see e.g. Liu et al., *Matl. Sci. Eng. C* 27(1):47-60 (January 2007); Yamada et al., *Chem. Lett.* 26(3):201-202 (1997); Fortier et al., *Biosens. Bioelectronics* 5:473-490 (1990)) as an extremely thin layer on an exposed face of the metal electrode, as shown in the FIGURE. Measuring in the direction perpendicular to the capillary length, the thickness of the applied layer may be e.g. 200 nm or less, 100 nm or less, or 50 nm or less, in selected embodiments.

In one embodiment, a mediator such as ferricyanide, as known in the art, is co-deposited along with the PPy and GOx. This system allows electrochemical measurement of the analyte to be carried out at a voltage of about 0.2-0.4V. A somewhat higher voltage (e.g. 0.7 V), which can lead to interference from other molecules in the interstitial fluid, would typically be required without the mediator. Other electron-accepting mediators known in the art for use with GOx include ferrocene derivatives, conducting organic salts such as tetrathiafulvalen-tetracycloquinodimethane (TTF-TCNQ), quinone compounds, phenothiazine compounds, and phenoxazine compounds.

The multilayer structure of the device containing the capillary channels can be fabricated by known deposition and etching methods. The sensing material 22 is, in one embodiment, applied by electrodeposition to one of the exposed edges of the gold electrode within the formed capillary channel 20, as noted above. As noted above, two noncontiguous edges of electrode are present within the microchannel, to allow for electrochemical detection. These edges could be visualized as two distinct semicircles within the inner surface of the channel, one of which is treated with the sensing material.

In use, a voltage is applied to the microheater sufficient to ablate the stratum corneum of the underlying skin, e.g. a voltage of about 3 V, typically for about 30 msec. This ablation (which typically produces a temperature of about 130° C.) allows interstitial fluid to enter the capillary channel, where it rises via capillary action and hydrostatic pressure and contacts the sensing material (e.g. PPy/GOx) within the capillary. A second voltage, typically 0.2-0.4 V, is then applied between the two above-described edge portions of the electrode layer), and the level of analyte (e.g. glucose) contacting the sensing material is electronically detected, preferably amperometrically detected, in accordance with known methods.

The device design presents various advantages, including the following. The sensor electrode pair, including the metal (e.g. gold) electrode and PPy/GOx-treated electrode (i.e. the two edge regions described above, one treated with sensor material), are located within the microcapillary channel and thus separated spatially from the microheater. This configuration avoids possible heat degradation of the enzyme. Further to this aspect, structural layer 14 is preferably formed of a heat-insulting material, such as a glass or ceramic material.

The detection of glucose is typically realized using chronoamperometry (measurement of current generated versus time for a voltage step). Ideally, every glucose molecule reaching the GOx sensing electrode should immediately release its electrons to produce the measured current. To achieve this condition, the electrode should have a low surface area to sample volume ratio, to ensure that glucose is not depleted in the vicinity of the sensing electrode during analysis. Accordingly, the sensing electrode is fabricated to be extremely small; i.e. essentially the width of the metal electrode layer 16, as shown in the FIGURE. Preferred thicknesses (measured in the direction perpendicular to the channel length) of the applied sensor layer 22 may be e.g. 200 nm or less, 100 nm or less, or 50 nm or less, in selected embodiments. in the 100 nm to 1 micron range, e.g. 500 nm. Diffusion times (i.e. the time for glucose molecules to reach the GOx enzyme) are reduced for similar reasons.

In general, the thickness of a metal layer applied via conventional metal deposition methods, e.g. electrodeposition or vapor deposition, can be precisely controlled, as compared to control of lateral dimensions of the planar surface area. Accordingly, high consistency in the effective sensor area (which is, again, the width dimension of the metal electrode layer 16), as well as roughness of the electrode layer, is achieved, giving high consistency between one sensor element and another, within a single device or between different devices. In fabrication of the multilayer device, the gold thickness can be easily reproduced with very little sidewall imperfections/roughness, and the exposed region (at the capillary wall) becomes the sensor electrode area.

Although glass/ceramic/polymeric substrate layers are exemplified, other materials, such as paper or other cellulose substrates, electrospun fibers, or other polymers, could also be used for the non-metal layers (12, 14, 18) in the device. However, surfaces contacting the skin, such as the lower surface of layer 12, should be non-absorbent and preferably hydrophobic in nature, in order to direct fluid flow from the skin into and though the capillary channel 20 to the sensing material 22. Methods of treating materials such as paper to render selected portions hydrophobic and/or non-absorbent are known in the art; see e.g. Martinez et al., *Anal. Chem.* 2010, 82, 3-10. The surface of structural layer 12 contacting the interior of the microchannel should be non-absorbent but should not repel water, so that sample fluid travels efficiently to the sensing area without volume loss.

Integrated circuitry (IC), including radio frequency (RF) communication capability, may be included peripheral to the device in order to transmit data readings to a remote location. By way of example, this transmission may employ Bluetooth™ devices, or it may be facilitated as part of a home area network (HAN) in a first instance, e.g., using protocols such as those described as part of the Zigbee standards. Further still, the data readings may be further transmitted outside of the HAN in accordance with a home health or telehealth communications system using existing wide area networks (WANs) such as the Internet.

One skilled in the art recognizes the other areas of application for the devices described herein. While the examples specifically described herein are directed to glucose monitoring, adaptations could be made to ascertain other information from the biomolecules and biomarkers in the interstitial fluid. For example, the individual sites could monitor for infectious disease (microbial, fungal, viral); hazardous compounds; heart or stroke indicators (troponin, C-reactive protein); chemical or biological toxins; cancer markers (PSA, estrogen); drug efficacy and dosing (metabolites): and the like. Such applications of the device as described are considered to be within the scope of the present invention.

The invention claimed is:

1. A sensing device comprising a plurality of individually controllable detection sites for electrochemically monitoring an analyte in interstitial fluid of a user, the device consisting of:
    a hydrophobic layer, designed to contact the skin;
    an overlaying first structural layer;
    an overlaying metal electrode layer;
    an overlaying second structural layer;
    for each such detection site, a dual opening capillary channel traversing these layers, thus providing an opening adjacent the skin;
    wherein said metal electrode layer is discontinuous at the circumference of said capillary channel, such that two non-contiguous edge portions of the metal electrode layer are present within the circumference of said channel;
    a first non-contiguous edge portion of the metal electrode layer including a sensing layer applied thereto effective to measure the analyte, the sensing layer being exposed to an interior of the capillary channel;
    microheater surrounding a lower end of said capillary channel, adjacent said hydrophobic layer, the microheater being effective to produce heat when a sufficient voltage is applied thereto sufficient to ablate the stratum corneum of the underlying skin, such that interstitial fluid containing the analyte enters the capillary channel and contacts the first non-contiguous edge portion of the metal electrode layer including the sensing layer.

2. The sensing device of claim 1, wherein the hydrophobic layer is silicone.

3. The sensing device of claim 1, wherein the first structural layer is selected from the group consisting of glass and a ceramic-like material.

4. The sensing device of claim 1, wherein the metal electrode layer is selected from the group consisting of gold and platinum.

5. The sensing device of claim 4, wherein the sensing layer is a conducting polymer.

6. The sensing device of claim 5, wherein the conducting polymer is polypyrrole (PPy).

7. The sensing device of claim 6, wherein the polypyrrole (PPy) is modified with glucose oxidase (GOx).

8. The sensing device of claim 7, wherein the polypyrrole (PPy) is modified with glucose oxidase (GOx) is co-deposited on the edge of the metal electrode layer with a mediator.

9. The sensing device of claim 8, wherein the mediator is ferricyanide.

10. A sensing device for electrochemically monitoring an analyte in interstitial fluid of a user, the device consisting of:
    a hydrophobic layer formed of silicone;
    a first thermally insulating structural layer formed on the hydrophobic layer;
    an electrode layer selected from the group of gold and platinum formed on the first structural layer;
    a second structural layer formed on the electrode layer;
    at least one capillary channel traversing these layers and having dual openings, including an opening adjacent the skin of the user;
    the electrode layer being discontinuous at the circumference of said capillary channel, such that two non-contiguous edge portions of electrode are present within the circumference of said channel;
    a first non-contiguous edge portion of the metal electrode layer including a sensing layer of polypyrrole (PPy) modified with glucose oxidase (GOx) applied thereto effective to measure the analyte in the interstitial fluid, the sensing layer being exposed to an interior of the capillary channel; and
    a microheater surrounding a lower end of said capillary channel, adjacent said hydrophobic layer, the microheater being effective to produce heat when a sufficient voltage is applied thereto sufficient to ablate the stratum corneum of the underlying skin, such that interstitial fluid enters the capillary channel and contacts the first non-contiguous edge portion of the metal electrode layer including the sensing layer.

* * * * *